US010543152B1

(12) United States Patent
Cotter et al.

(10) Patent No.: US 10,543,152 B1
(45) Date of Patent: Jan. 28, 2020

(54) METHOD AND APPARATUS FOR PROVIDING PRESCRIPTION VERIFICATION

(71) Applicant: WALGREEN CO., Deerfield, IL (US)

(72) Inventors: Nichole R. Cotter, Buffalo Grove, IL (US); Donnamarie A. Christie, Orlando, FL (US); Averill D. Gordon, Grayslake, IL (US)

(73) Assignee: WALGREEN CO., Deerfield, IL (US)

( * ) Notice: Subject to any disclaimer, the term of this patent is extended or adjusted under 35 U.S.C. 154(b) by 717 days.

(21) Appl. No.: 14/521,236

(22) Filed: Oct. 22, 2014

(51) Int. Cl.
G16H 40/20 (2018.01)
A61J 7/00 (2006.01)
G05B 15/02 (2006.01)

(52) U.S. Cl.
CPC ............ A61J 7/0076 (2013.01); G05B 15/02 (2013.01)

(58) Field of Classification Search
None
See application file for complete search history.

(56) References Cited

U.S. PATENT DOCUMENTS

| 5,628,530 | A | 5/1997 | Thornton |
| 5,832,449 | A | 11/1998 | Cunningham et al. |
| 6,529,892 | B1 | 3/2003 | Lambert |
| 6,859,780 | B1 | 2/2005 | Cunningham |
| 6,978,286 | B2 | 12/2005 | Francis et al. |
| 6,993,402 | B2 | 1/2006 | Klass et al. |
| 7,014,063 | B2 | 3/2006 | Shows et al. |
| 7,020,697 | B1 | 3/2006 | Goodman et al. |
| 2002/0143582 | A1 | 10/2002 | Neuman et al. |
| 2003/0074225 | A1* | 4/2003 | Borsand ................ G06F 19/328 705/3 |
| 2003/0125983 | A1 | 7/2003 | Flack et al. |
| 2003/0144884 | A1 | 7/2003 | Mayaud |
| 2003/0167190 | A1 | 9/2003 | Rincavage et al. |
| 2004/0059600 | A1 | 3/2004 | Ball et al. |
| 2004/0088187 | A1* | 5/2004 | Chudy ................... G06Q 10/10 705/2 |
| 2004/0148195 | A1 | 7/2004 | Kalies |
| 2005/0033610 | A1 | 2/2005 | Cunningham |
| 2005/0060197 | A1 | 3/2005 | Mayaud |

(Continued)

OTHER PUBLICATIONS

Wikipedia, Route of admiistration, Aug. 8, 2013. https://en.wikipedia.org/w/index.php?title=Route_of_administration&oldid=567615559 (Year: 2013).*

(Continued)

Primary Examiner — Aryan E Weisenfeld
Assistant Examiner — Joshua B Blanchette
(74) Attorney, Agent, or Firm — Marshall, Gerstein & Borun LLP

(57) ABSTRACT

A system, apparatus, and method for providing an auditing feature capable of verifying a prescription has been correctly dispensed by a pharmacy are disclosed. More particularly, embodiments of the present invention relate to a system, apparatus, and/or method for automatically checking a customer's prescription information against known information related to the customer and/or the prescription contents in order to verify that the dispensed prescription is correct. It follows that an attentive and accurate dispensing process may be made available for a pharmacy to dispense prescriptions.

19 Claims, 10 Drawing Sheets

(56) References Cited

U.S. PATENT DOCUMENTS

| | | |
|---|---|---|
| 2005/0071193 A1 | 3/2005 | Kalies |
| 2005/0080651 A1 | 4/2005 | Morrison et al. |
| 2005/0090425 A1 | 4/2005 | Reardan et al. |
| 2005/0154627 A1 | 7/2005 | Zuzek et al. |
| 2006/0098193 A1 | 5/2006 | Rzasa et al. |
| 2006/0161294 A1 | 7/2006 | DiMaggio |
| 2007/0088565 A1* | 4/2007 | Berkelhamer ......... G16H 40/20 705/2 |
| 2007/0100662 A1 | 5/2007 | Suwalski et al. |
| 2007/0214014 A1* | 9/2007 | Suwalski ............ G06F 19/3456 705/3 |
| 2013/0211847 A1* | 8/2013 | Vaidya ................... G06Q 50/22 705/2 |
| 2014/0136231 A1 | 5/2014 | Suwalski et al. |
| 2015/0347715 A1* | 12/2015 | Tilzer ................... G06F 16/951 705/2 |

OTHER PUBLICATIONS

Mekhjian et al., "Development of a Web-based Event Reporting System in an Academic Environment", Journal of the American Medical Informatics Association; Jan./Feb. 2004; 11, 1; pp. 11-18.
The Institute for Safe Medication Practices. ISMP List of Error-Prone Abbreviations, Symbols, and Dose Designations and ISMP's list of high-alert medications. Accessed on Mar. 23, 2009 at http://web.archive/org/web/20050515210418/www.ismp.org/PDF?ErrorProne.pdf and http://web.archive.org/web/20050315165646/www.ismp.org/MSAarticles/highalert.htm.
Unpublished pending U.S. Appl. No. 14/845,489, filed on Sep. 4, 2015, a copy of which is not being furnished herewith, pursuant to the Commissioner's Notice dated Sep. 21, 2004 (19US2).
Unpublished pending U.S. Appl. No. 14/516,214, filed Oct. 16, 2014, a copy of which is not being furnished herewith, pursuant to the Commissioner's Notice dated Sep. 21, 2004 (19US2).

* cited by examiner

40

| Description of Identified Issue | Audit Type | Description of Audit Rule Violated |
|---|---|---|
| Topical Metronidazole should not be inserted vaginally. Please clarify. | Quality Audit | Captures prescriptions verified for a topical metronidazole product with directions to use vaginally. |
| Ear drops should not be used in the eye. Please clarify. | Quality Audit | Captures prescriptions verified for an otic preparation with directions to use in the eye. |
| Conflicting routes of administration in directions. | Quality Audit | Captures prescription verified for a nasal or oral inhaler with directions to use by mouth and nasally. |
| Incorrect route of administration. Nasal inhaler with directions to use orally. Please clarify. | Quality Audit | Captures prescriptions verified for a nasal inhaler with directions to use by mouth. |
| Incorrect route of administration. Oral inhaler with directions to use nasally. Please clarify. | Quality Audit | Captures prescriptions verified for an oral inhaler with directions to use nasally. |
| Byetta 10mcg pens cannot deliver 5mcg. Clarify if MD would like the patient to use the 5mcg pens. Byetta is dosed in MCG only. | Quality Audit | Captures prescriptions verified for Byetta 10 MCG Pens with directions to inject 5 MCG, a dosage the device cannot deliver. |
| Byetta pens cannot deliver 250mcg. Clarify dosage with MD. | Quality Audit | Captures prescriptions verified for Byetta Pens, either strength, with directions to inject 250 MCG, a dosage the device cannot deliver. |
| Invalid dosage. Based on dose (1.2ML) this indicates that the entire pen would be injected as a single dose. Also, Byetta is dosed in MCG only. | Quality Audit | Captures prescriptions verified for Byetta Pens, either strength, with directions to inject 1.2 ML, the package size for the entire 5 MCG pen. |
| Invalid dosage. Based on dose (2.4ML) this indicates that the entire pen would be injected as a single dose. Also, Byetta is dosed in MCG only. | Quality Audit | Captures prescriptions verified for Byetta Pens, either strength, with directions to inject 2.4 ML, the package size for the entire 10 MCG pen. |
| The MCG to ML conversion is incorrect, should be 0.04ML however, Byetta pens display and is dosed in MCG only. Also, Byetta 5mcg pens cannot deliver 10 mcg. Clarify if MD would like the patient to use the 10mcg pens. | Quality Audit | Captures prescriptions verified for Byetta 5 MCG Pens with directions to inject 0.4 ML instead of 0.04 ML (10 MCG) and instructs the store to clarify the strength with the prescriber. |
| The MCG to ML conversion is incorrect, should be 0.04ML however, Byetta pens display and is dosed in MCG only. Please clarify and remove the ML conversion. | Quality Audit | Captures prescriptions verified for Byetta 10 MCG Pens with directions to inject 0.4 ML instead of 0.04 ML (10 MCG) and instructs the store to express the dosage in MCG. |
| The MCG to ML conversion is incorrect, should be 0.02ML however, Byetta pens display and is dosed in MCG only. Please clarify and remove the ML conversion. | Quality Audit | Captures prescriptions verified for Byetta 5 MCG Pens with directions to inject 0.2 ML instead of 0.02 ML (5 MCG) and instructs the store to express the dosage in MCG. |

| Description of Identified Issue | Audit Type | Description of Audit Rule Violated |
|---|---|---|
| The MCG to ML conversion is incorrect should be 0.02ML however, Byetta pens display and is dosed in MCG only. Also, Byetta 10mcg pens cannot deliver 5mcg. Clarify if MD would like the patient to use the 5mcg pens. | Quality Audit | Captures prescriptions verified for Byetta 10 MCG Pens with directions to inject 0.2 ML instead of 0.02 ML (5 MCG) and instructs the store to clarify the strength with the prescriber as this device is not able to deliver a 5 MCG dosage. |
| MG dosing is incorrect. Byetta pens display and is dosed in MCG only. | Quality Audit | Captures prescriptions verified for Byetta Pens, either strength, with directions containing a dosage expressed in MG or MILLIGRAMS. |
| Incorrect route of administration. Vagifem Tabs should be inserted vaginally, not taken orally. | Quality Audit | Captures prescriptions verified for Estradiol Vaginal Tablets (Vagifem) with directions to use by mouth. |
| MG dosing is incorrect. SymlinPens display and is dosed in MCG only. | Quality Audit | Captures prescriptions verified for Symlin Pens, either strength, with directions containing a dosage expressed in MG or MILLIGRAMS |
| Incorrect Dosage. Symlin 120mcg Pens only dispense 60mcg and 120mcg dosages. | Quality Audit | Captures prescriptions verified for Symlin 120 MCG Pens with directions to inject a dosage the device cannot deliver. |
| Incorrect Dosage. Symlin 60mcg Pens only dispense 15mcg, 30mcg, 45mcg and 60mcg dosages. | Quality Audit | Captures prescriptions verified for Symlin 60 MCG Pens with directions to inject a dosage the device cannot deliver. |
| SymlinPen only displays MCG increments and should not be converted to ML. | Quality Audit | Captures prescriptions verified for Symlin Pens, either strength, with directions containing a dosage expressed in ML or MILLILITERS. |
| Invalid dosage. Based on dose (18ML) this indicates that 6 pens would be injected as a single dose. Please clarify. | Quality Audit | Captures prescriptions verified for Victoza Pens with directions to inject 18 ML, a dosage the device cannot deliver. |
| Invalid dosage. Based on dose (18MG) this indicates that the entire pen would be injected. Please clarify. | Quality Audit | Captures prescriptions verified for Victoza Pens with directions to inject 18 MG, a dosage the device cannot deliver. |
| Invalid dosage. Based on dose (3ML) this indicates that the entire pen would be injected. Please clarify. | Quality Audit | Captures prescriptions verified for Victoza Pens with directions to inject 3 ML, a dosage the device cannot deliver. |
| Invalid Dosage. Each Victoza pen delivers doses of 0.6mg, 1.2mg and 1.8mg. | Quality Audit | Captures prescriptions verified for Victoza Pens with directions to inject a dosage the device cannot deliver. |
| This device is dosed in MG increments only and should not be converted to ML. Victoza pens only delivers 0.6MG, 1.2MG and 1.8MG dosages. | Quality Audit | Captures prescriptions verified for Victoza Pens with directions containing a dosage expressed in ML or MILLILITERS. |

| Description of Identified Issue | Audit Type | Description of Audit Rule Violated |
|---|---|---|
| Incorrect drug verified. Direction or indication suggests this should be HYDROXYZINE. | Quality Audit | 1) Captures prescriptions verified for Hydralazine with directions containing an indication normally prescribed for Hydroxyzine.<br>2) Captures prescriptions verified for HCTZ with directions containing frequencies and/or indication normally prescribed for Hydroxyzine.<br>*Note: The brand/generic equivalents for the drugs used in this rule are not included.* |
| Incorrect frequency. Fosamax 70mg Tablets are normally dosed once per week. Please clarify. | Quality Audit | Captures prescriptions verified for Alendronate 70 MG Tablets with directions to use daily. |
| Unusual dosage. Zolpidem is dosed at bedtime. | Quality Audit | Captures prescriptions verified for Zolpidem products with directions to use in the morning. |
| Incorrect frequency. Clonidine/Catapres Patches are applied once weekly. Please clarify. | Quality Audit | Captures prescriptions verified for Clonidine Patches with directions to use daily. |
| Incorrect drug strength. The 0.65ml pkg size is for the 104mg injection. | Quality Audit | Captures prescriptions verified for Medroxyprogesterone 150 MG Injections with directions to inject 0.65 ML, the package size for the 104 MG strength. |
| Incorrect route of administration. DepoProvera 150 is injected intramuscularly to be effective. | Quality Audit | Captures prescriptions verified for Medroxyprogesterone 150 MG Injections with directions to inject dose under the skin. |
| Incorrect frequency. DepoProvera 150mg Injections are normally dosed every 3 months. Please clarify. | Quality Audit | Captures prescriptions verified for Medroxyprogesterone 150 MG Injections with directions containing a frequency other than every 3 months. |
| Incorrect dosage and/or frequency. Dosages greater than manufacturer recommended ONE INHALATION FROM ONE CAPSULE ONCE DAILY must be clarified with prescriber and documented Review the days of supply to make sure 30 capsules (1 package) is equal to a 30 days of supply using the manufacturer recommended dosing. | Quality Audit | Captures prescriptions verified for Spiriva with directions containing a frequency greater than once daily or a dosage greater than one capsule. |
| Update the directions to include "Inhale the contents of 1 capsule via handihaler" (be sure to include the frequency). These capsules are not oral capsules, they are oral INHALATION capsules. | Quality Audit | Captures prescriptions verified for Spiriva with directions instructing the patient to TAKE the medication instead of INHALING. |

| Description of Identified Issue | Audit Type | Description of Audit Rule Violated |
|---|---|---|
| The directions are misleading or verified incorrectly. "FOR 7 DAYS" suggests daily use. Please update to "EVERY 7 DAYS." | Quality Audit | Captures prescriptions verified for Methotrexate Tablets with directions containing the typo "FOR 7 DAYS" instead of "EVERY 7 DAYS". |
| Clarify Directions for Methotrexate: Methotrexate therapy should be WEEKLY and not daily use. Clarify with prescriber and document prescription, even if prescription written for daily use. | Quality Audit | Captures prescriptions verified for Methotrexate: <br> 1) with a day supply that is a multiple of 7 (up to 84 days) and directions containing a once daily frequency. <br> 2) with directions containing a dosage greater than 1 tablet and a once daily frequency. |
| Diastat should not be dosed in ML. Diastat 2.5mg only dispenses 2.5mg. | Quality Audit | Captures prescriptions verified for Diastat 2.5 MG Rectal Gel with directions containing a dosage expressed in ML or MILLILITERS. |
| Diastat should not be dosed in ML. Diastat 10mg only dispenses 5mg, 7.5mg and 10mg dosages. | Quality Audit | Captures prescriptions verified for Diastat 10 MG Rectal Gel with directions containing a dosage expressed in ML or MILLILITERS. |
| Diastat should not be dosed in ML. Diastat 20mg only dispenses 10mg, 12.5mg, 15mg, 17.5mg and 20mg dosages. | Quality Audit | Captures prescriptions verified for Diastat 20 MG Rectal Gel with directions containing a dosage expressed in ML or MILLILITERS. |
| Invalid dosage. Diastat 2.5mg only dispenses a 2.5mg dose. | Quality Audit | Captures prescriptions verified for Diastat 2.5 MG Rectal Gel with directions containing a dosage the device cannot deliver. |
| Invalid dosage. Diastat 10mg only dispenses 5mg, 7.5mg and 10mg dosages. | Quality Audit | Captures prescriptions verified for Diastat 10 MG Rectal Gel with directions containing a dosage the device cannot deliver. |
| Invalid dosage. Diastat 20mg only dispenses 10mg, 12.5mg, 15mg, 17.5mg and 20mg dosages. | Quality Audit | Captures prescriptions verified for Diastat 20 MG Rectal Gel with directions containing a dosage the device cannot deliver. |
| Incorrect strength selected. The correct strength is the 0.15mg, which is EPIPEN JR. | Quality Audit | Captures prescriptions verified for Epipen 0.3 MG for a patient less than 2 years old. |
| Incorrect strength selected. The correct strength is the 0.15mg, which is AUVI-Q 0.15MG AUTO-INJECTOR 2 PACK. | Quality Audit | Captures prescriptions verified for Auvi-Q 0.3 MG for a patient less than 2 years old. |
| Incorrect frequency. Normal dosage is to insert 1 ring vaginally and replace after 3 months. Please clarify. | Quality Audit | Captures prescriptions verified for Femring with directions containing a once daily frequency. |

| Description of Identified Issue | Audit Type | Description of Audit Rule Violated |
|---|---|---|
| Incorrect route of administration. EVAMIST is a topical hormone product to be applied to the forearm. | Quality Audit | Captures prescriptions verified for Evamist Topical Spray with directions to use nasally. |
| Incorrect drug verified. This prescription should be for CLOMID or CLOMIPHENE. | Quality Audit | Captures prescriptions verified for Clomipramine with directions containing verbiage that can be applied to Clomiphene. |
| Incorrect dosage and route of administration. Nascobal/Calomist is 0.1ML per dose and used intranasally. | Quality Audit | Captures prescriptions verified for Cyanocobalamin Spray with directions to use by mouth and a dosage expressed in ML, excluding 0.1 ML. |
| Incorrect dosage. Nascobal/Calomist is 0.1ML per dose. | Quality Audit | Captures prescriptions verified for Cyanocobalamin Spray with directions containing a dosage expressed in ML, excluding 0.1 ML. |
| Incorrect route of administration. Nascobal/Calomist is used intranasally. | Quality Audit | Captures prescriptions verified for Cyanocobalamin Spray with directions to use by mouth. |
| Clarify frequency. Nascobal is normally dosed once weekly. | Quality Audit | Captures prescriptions verified for Nascobal with directions containing a once daily frequency. |
| Verify frequency. Actonel 35MG is normally dosed once per week. | Quality Audit | Captures prescriptions verified for Actonel 35 MG Tablets with directions containing a once daily frequency. |
| Verify frequency. Actonel 150MG is normally dosed once per month. | Quality Audit | Captures prescriptions verified for Actonel 150 MG Tablets with directions containing a once daily frequency. |
| Incorrect frequency. Butrans is not dosed daily, please clarify. | Quality Audit | Captures prescriptions verified for Butrans Patches, any strength, with directions containing a once daily frequency. |
| Incorrect route of administration and frequency. Bydureon is administered subcutaneously and dosed once weekly, please clarify. | Quality Audit | Captures prescriptions verified for Bydureon Injections with directions to inject into the muscle and a once daily frequency. |
| Incorrect frequency. Bydureon is dosed once weekly, please clarify. | Quality Audit | Captures prescriptions verified for Bydureon Injections with directions containing a once daily frequency. |
| Incorrect route of administration. Bydureon is administered subcutaneously. | Quality Audit | Captures prescriptions verified for Bydureon Injections with directions to inject under the skin. |
| Incorrect frequency. Climara Patches are normally applied once weekly, please clarify. | Quality Audit | Captures prescriptions verified for Climara Patches, any strength, with directions containing a once daily frequency. |

| Description of Identified Issue | Audit Type | Description of Audit Rule Violated |
|---|---|---|
| Incorrect route of administration and frequency. Enbrel is administered subcutaneously and dosed once weekly, please clarify. | Quality Audit | Captures prescriptions verified for Enbrel Injections with directions to inject into the muscle and a once daily frequency. |
| Incorrect frequency. Enbrel is dosed once weekly, please clarify. | Quality Audit | Captures prescriptions verified for Enbrel Injections with directions containing a once daily frequency. |
| Incorrect route of administration. Enbrel is administered subcutaneously. | Quality Audit | Captures prescriptions verified for Enbrel Injections with directions to inject into the muscle. |
| Incorrect route of administration and frequency. Pegasys is administered subcutaneously and dosed once weekly based on MOA, please clarify. | Quality Audit | Captures prescriptions verified for Pegasys Injections with directions to inject into the muscle and a once daily frequency. |
| Incorrect frequency. Pegasys is dosed once weekly based on MOA, please clarify. | Quality Audit | Captures prescriptions verified for Pegasys Injections with directions containing a once daily frequency. |
| Incorrect route of administration. Pegasys is administered subcutaneously. | Quality Audit | Captures prescriptions verified for Pegasys Injections with directions to inject into the muscle. |
| Incorrect route of administration and frequency. Humira is administered subcutaneously and is not dosed daily, please clarify. | Quality Audit | Captures prescriptions verified for Humira Injections with directions to inject into the muscle and a once daily frequency. |
| Incorrect frequency. Humira is not dosed daily, please clarify. | Quality Audit | Captures prescriptions verified for Humira Injections with directions containing a once daily frequency. |
| Incorrect route of administration. Humira is administered subcutaneously. | Quality Audit | Captures prescriptions verified for Humira Injections with directions to inject into the muscle. |
| Incorrect route of administration and frequency. Ortho Evra Patches are applied topically (not for oral use) and normally applied once weekly, please clarify. | Quality Audit | Captures prescriptions verified for Ortho Evra Patches with directions to use by mouth and a once daily frequency. |
| Incorrect frequency. Ortho Evra Patches are normally applied once weekly, please clarify. | Quality Audit | Captures prescriptions verified for Ortho Evra Patches with directions containing a once daily frequency. |
| Incorrect route of administration. Ortho Evra Patches are applied topically and not for oral use. | Quality Audit | Captures prescriptions verified for Ortho Evra Patches with directions to use by mouth. |

| Description of Identified Issue | Audit Type | Description of Audit Rule Violated |
|---|---|---|
| Incorrect route of administration and frequency. Estradiol Patches are applied topically (not for oral use) and normally applied once weekly, please clarify. | Quality Audit | Captures prescriptions verified for Estradiol Patches with directions to use by mouth and a once daily frequency. |
| Incorrect frequency. Estradiol Patches are normally applied once weekly, please clarify. | Quality Audit | Captures prescriptions verified for Estradiol Patches with directions containing a once daily frequency. |
| Incorrect route of administration. Estradiol Patches are applied topically and not for oral use. | Quality Audit | Captures prescriptions verified for Estradiol Patches with directions to use by mouth. |
| Incorrect frequency. Vivelle Patches are normally applied twice weekly, please clarify. | Quality Audit | Captures prescriptions verified for Vivelle Patches with directions containing a once daily frequency. |
| Combivent Respimat has a different dosing regimen. Manufacturer Recommended frequency = 1 puff PO QID (Maximum Daily Dose: 6 puffs per day). Please contact prescriber to clarify formulation and dosing regimen. | Quality Audit | Captures prescriptions verified for Combivent Respimat with directions containing a daily dose greater than 6 puffs per day. |
| Refills cannot be authorized for hydrocodone products due to Oklahoma state law. | Compliance Audit | Captures prescriptions verified for Hydrocodone products (that fall in 38 GPI specified by legal) with refills in Oklahoma. |
| Child under 2 years old. Please clarify dosage for Zantac/Ranitidine Syrup and annotate the prescription. | Quality Audit | Captures prescriptions verified for Ranitidine Oral Syrup with directions containing a dosage of 15 ML, a typo, for patients less than 2 years old. |
| Zohydro ER frequency is to be no more than EVERY 12 HOURS and PRN should NOT be indicated in the directions. Please clarify directions with prescriber. | Quality Audit | Captures prescriptions verified for Zohydro ER Tablets, all strengths, with directions containing PRN and a frequency greater than twice daily. |
| Zohydro ER is not indicated as an as-needed (PRN) analgesic. Clarify with prescriber to inform PRN is not to be indicated in directions per manufacturers recommendation. | Quality Audit | Captures prescriptions verified for Zohydro ER Tablets, all strengths, with directions containing PRN. |
| Zohydro ER frequency is to be no more than EVERY 12 HOURS. Please clarify frequency with prescriber. | Quality Audit | Captures prescriptions verified for Zohydro ER Tablets, all strengths, with directions containing a frequency greater than twice daily. |

FIGURE 10

METHOD AND APPARATUS FOR PROVIDING PRESCRIPTION VERIFICATION

TECHNICAL FIELD

Embodiments of the present invention generally relate to a system, apparatus, and method for providing an auditing feature capable of validating a prescription has been correctly dispensed by a pharmacy. More particularly, embodiments of the present invention relate to a system, apparatus, and/or method for automatically checking a customer's prescription information against known information related to the customer and/or the prescription contents in order to validate that the dispensed prescription is correct. It follows that an attentive and accurate dispensing process is made available for a pharmacy to dispense prescriptions.

BACKGROUND

Patients may be prescribed medication by a medical doctor to address certain ailments the patient may be suffering. In order to then obtain the medication prescribed by the medical doctor, the patient must generally have the prescription filled through a pharmacy, either at a medical facility or retail location. Therefore, the process generally followed by a patient to fill a prescription includes the patient receiving a prescription from a medical doctor, the patient presenting the prescription to a pharmacy, and the pharmacy filling the prescription by identifying the medication described in the prescription and dispensing the medication to the patient. In addition, the pharmacy may provide directions to the patient for taking the medication contents described in the prescription.

Some prescription filling systems may include failsafe protocols that look to confirm that the medication described in the patient's prescription matches the medication dispensed by the pharmacy before the medication is released to the patient from the pharmacy. Some prescription filling systems may also include a warning notification feature that provides the pharmacist with one or more notifications describing known adverse effects of the medication.

SUMMARY

The present disclosure describes a system, apparatus, and method configured to provide a detailed audit on a patient's prescription that has been filled by a pharmacy, or is in the process of being filled by a pharmacy. According to some embodiments, the audit features of the present invention will include checking one or more of the patient's profile history, prescription notes, prescription filling information, a database of known usage criteria, and/or third party billing requirements in order to validate that the medication that has been filled, or is in the process of being filled, by the pharmacy is the correct medication for the patient and/or that the correct billing criteria has been applied. Further, according to some embodiments when the auditing features of the present invention triggers an alert that the medication filled by the pharmacy for dispensing to the patient may not be correct, a hard stop may be implemented that requires an express action to be taken before the medication can be dispensed/released to the patient, and/or requires someone to contact the customer to inform the customer as to an incorrect medication that the customer may have been dispensed.

According to some embodiments of the invention described herein, a computing device for auditing a prescription filling order of a prescription processed by an order filling device located at a pharmacy. The computing device may comprise a communication interface configured to receive prescription information from the order filling device, the prescription information describing information included in the prescription of the prescription filling order; a memory configured to store known information; and a processor in communication with the communication interface and memory. The processor may be configured to: receive the prescription information; receive the known information from the memory; analyze the prescription information and the known information; and determine an issue exists based on the analysis.

According to some embodiments of the invention described herein, a method for auditing a prescription filling order of a prescription processed by an order filling device located at a pharmacy. The method may comprise receiving, by a processor, prescription information from the order filling device through a communication interface, the prescription information describing information included in the prescription of the prescription filling order; receiving, by the processor, known information stored on a memory; analyzing, by the processor, the prescription information and the known information; and determining, by the processor, an issue exists based on the analysis.

These and various other embodiments and aspects will become apparent and be more fully understood from the following detailed description and accompanying drawings, which set forth the illustrative embodiments that are indicative of the various ways in which the principles of the invention may be employed.

This application is defined by the appended claims. The description summarizes aspects of the embodiments and should not be used to limit the claims. Other implementations are contemplated in accordance with the techniques described herein, as will be apparent upon examination of the following drawings and detailed description, and such implementations are intended to be within the scope of this application.

BRIEF DESCRIPTION OF THE DRAWINGS

For a better understanding of the invention, reference may be made to embodiments shown in the following drawings. The components in the drawings are not necessarily to scale and related elements may be omitted so as to emphasize and clearly illustrate the novel features described herein. In addition, system components can be variously arranged, as known in the art. In the figures, like referenced numerals may refer to like parts throughout the different figures unless otherwise specified.

FIG. 4 illustrates an exemplary table that may be included in a database that identifies auditing rules, according to some embodiments;

FIG. 5 illustrates an exemplary table that may be included in a database that identifies auditing rules, according to some embodiments;

FIG. 6 illustrates an exemplary table that may be included in a database that identifies auditing rules, according to some embodiments;

FIG. 7 illustrates an exemplary table that may be included in a database that identifies auditing rules, according to some embodiments;

FIG. 8 illustrates an exemplary table that may be included in a database that identifies auditing rules, according to some embodiments;

FIG. 9 illustrates an exemplary table that may be included in a database that identifies auditing rules, according to some embodiments; and FIG. 10 illustrates an exemplary table that may be included in a database that identifies auditing rules, according to some embodiments.

DETAILED DESCRIPTION OF EXAMPLE EMBODIMENTS

Figure 1:
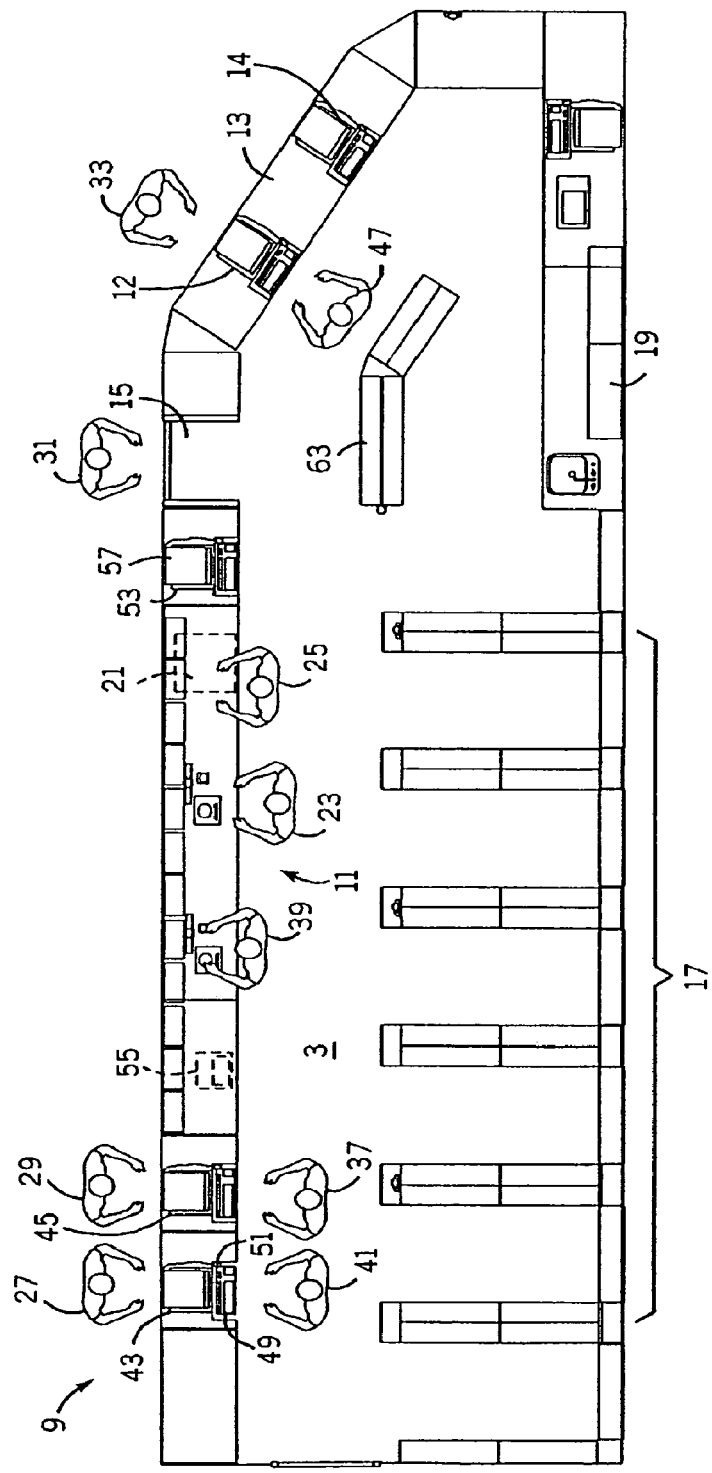
FIG. 1 illustrates an exemplary schematic diagram for a pharmacy operation environment, according to some embodiments.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated. Not all of the depicted components described in this disclosure may be required, however, and some implementations may include additional, different, or fewer components from those expressly described in this disclosure. Variations in the arrangement and type of the components may be made without departing from the spirit or scope of the claims as set forth herein.

The "dispensing" of medication for a prescription involves a process for entering, filling, verifying and selling the medication described in the prescription. During this process, errors and/or mix-ups may occur that may result in the wrong medication being dispensed to a customer. It follows that embodiments of the present invention are directed to preventing particular pharmacy error events, such as internal pharmacy error events, which may result in a customer being dispensed the wrong medication. A pharmacy error event is any occurrence that prevents the pharmacy from filling a prescription correctly, and can include at least dispensing a prescription with incorrect directions for a particular drug, dispensing a medication or drug that does not match a medication or drug identified in the prescription, dispensing a medication or drug identified in the prescription but mistakenly written by a doctor who has written the prescription, and/or dispensing a medication or drug without informing the customer as to particular requirements for such medication or drug. In addition to the exemplary pharmacy errors described, the features described herein may be configured to account for other types of pharmacy errors that can occur during the process of dispensing medication.

Embodiments of the present invention are directed to auditing a prescription filling process in order to check whether certain types of errors have occurred before the prescription dispensing, during the prescription dispensing, or after the prescription dispensing in order to provide one or more remedial actions to address the identified errors. The features of the present invention may be located and used in any environment wherein medications are dispensed in order to fill prescription orders, where human intervention in the order-filling process takes place. Thus, the term "pharmacy" is intended to include diverse environments including retail pharmacies, pharmacies in alternate site facilities, hospital pharmacies and the like.

The improved pharmacy management system 1 according to this disclosure will be described with respect to an exemplary and conventional pharmacy layout illustrated in FIG. 1. Specifically, referring now to FIG. 1, a conventional pharmacy 3 shown therein includes an order entry workstation 9, a filling/checking workstation 11, a payment workstation 13 and a consultation workstation 15. Conventional pharmacy 3 is provided with any number of non-automated storage locations at which medications and products are stored for access by pharmacy personnel. For example, the pharmacy 3 shown in FIG. 1 is provided with an array of six static storage shelf units 17. Each storage shelf unit within the array 17 is typically about 6 to 8 feet in height and includes a plurality of spaced-apart horizontally-oriented shelves. Medications and products are stored on each shelf within the array 17 pending manual retrieval for fulfillment of a prescription order.

Pharmacy 3 may include other storage locations such as a restricted-access cabinet 19 for storage of narcotics and other controlled medications. Pharmacy 3 may also include a refrigerator 21 for storage of perishable medications and articles.

Pharmacy 3 is staffed by personnel having varying levels of responsibility. The pharmacy staff includes at least one registered pharmacist 23, 25. Each pharmacist (e.g., pharmacist 23) is responsible for fulfillment of prescription orders and for verification of each prescription order before the order is provided to a customer 27, 29, 31, or 33. One or more filling technicians 37, 39 may be employed to assist pharmacists 23, 25 in fulfilling each prescription order. The pharmacists 23, 25 or filling technicians 37, 39 may also provide health-care-related information to a customer 31 at consultation station 15.

A data entry clerk or technician 41 is provided to supply prescription order information to a host computer and pharmacy information system (not shown) via computer terminal 43 or 45 at data entry station 9. A sales clerk 47 processes sales transactions at the payment workstation 13 using computer terminal 14 or 16.

Workflow at conventional pharmacy 3 may be summarized in the following manner. Data entry clerk or technician 41, pharmacist 23, 25, technician 37, 39, or other pharmacy staff may receive a prescription order from a customer 27, 29, 31, or 33 and then input the prescription order information to the system at data entry workstation 9 using keyboard 49, computer mouse 51, or other available input command component of computer 43. Following adjudication by the pharmacy information system, each adjudicated order is held in a database on pharmacy computer 53 at filling/checking workstation 11 for fulfillment, typically on a first in first out ("FIFO") basis. Labels for attachment to each container associated with the prescription order may be printed on printer 55.

Pharmacist 23, 25 or filling technician 37, 39 selects the prescription order next in line to be filled from the pharmacy computer 53 of the filling/checking workstation 11. The prescription order, and prescriptions comprising the order, may be displayed on a communications device, such as a display 57 associated with computer 53. The prescriptions making up the prescription orders may be arranged in an order automated by the computer 53, or may not be arranged in any particular sequence.

The pharmacist 23, 25 or filling technician 37, 39 then fills each prescription in the prescription order. Each prescription in the prescription order is filled by walking to one of the storage locations 17-21 and retrieving the appropriate medication which may be in bulk-form or in prepackaged form. The medication is then taken from the storage location 17-21 to the filling/checking work station 11 where the appropriate number of medications are metered into a container, such as a vial, bottle with reclosable cap, box or other type of container capable of holding the medication as intended.

This process is repeated until each prescription in the prescription order is fulfilled. The prescription order is then verified by pharmacist 23, 25 at filling/checking work station 11 to ensure that the correct medication is in each container (e.g., vial, bottle, box, etc.). The fulfilled order may then be placed in a bag or other package and is held at a "will call" area 63 near payment work station 13. Sales clerk 47 processes the transaction and delivers the packaged prescription order to customer 33 at the payment work station 13.

The description of the pharmacy 3 is provided for exemplary purposes only in accordance to some embodiments. It follows that it is within the scope of the innovation described herein to include other embodiments where the pharmacy 3 may include a fewer, or greater, number of components, stations, or employees. For instance, the pharmacy may additionally include a drive-up window such that any one or more of the order entry workstation 9, filling/checking workstation 11, payment workstation 13 and/or consultation workstation 15 may be available at the drive-up window. By including the additional drive-up window, a customer may fill their prescription at the pharmacy 3 without having to leave their vehicle.

Figure 2:
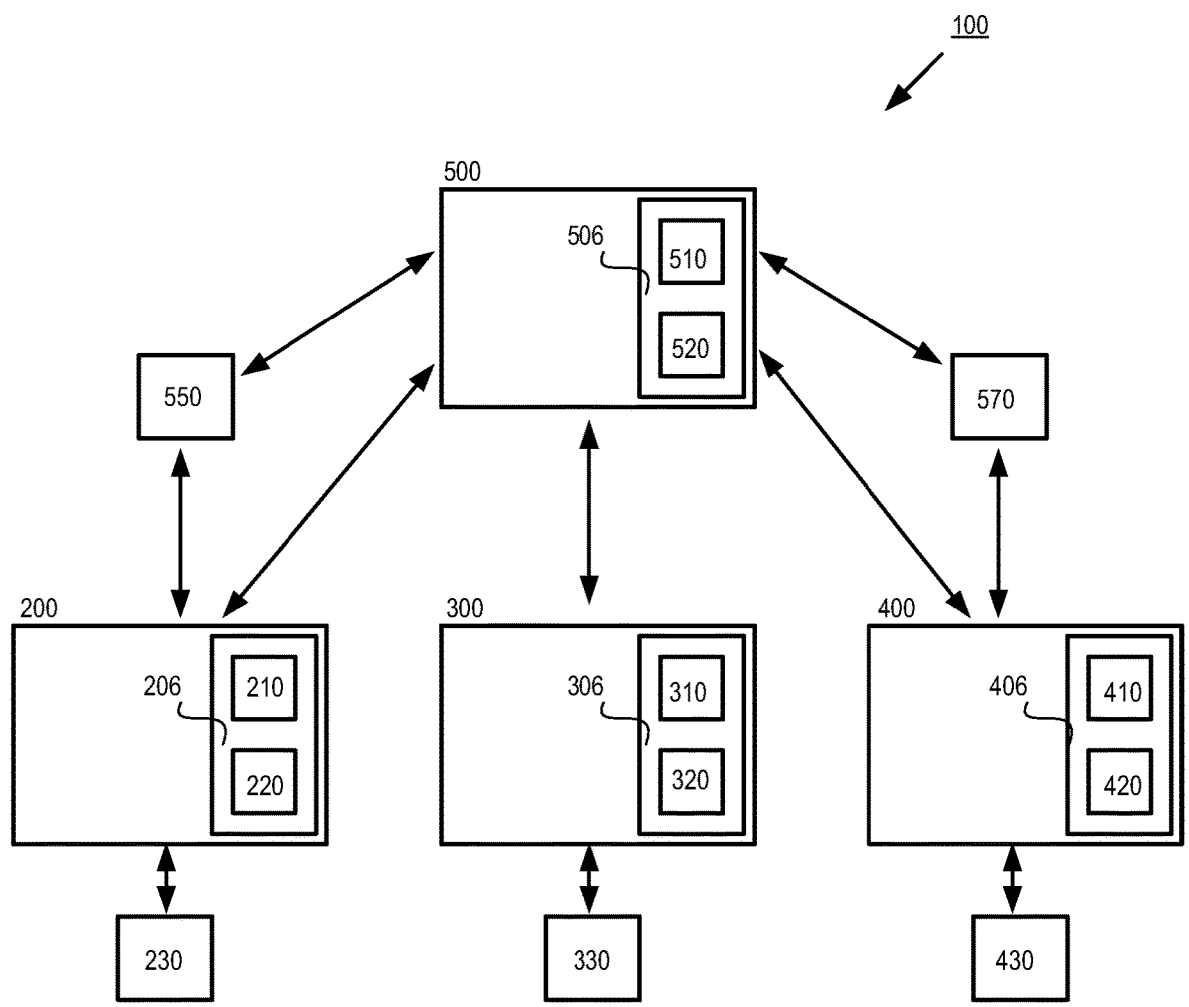
FIG. 2 illustrates an exemplary schematic diagram for a pharmacy management system, according to some embodiments.

Referring to FIG. 2, there is shown a pharmacy management system 100 for efficiently entering, filling and dispensing prescriptions in an integrated manner in relation to the distribution of medication to patients through a single or multi-store pharmacy operation. As shown in FIG. 2, a single or multi-server based arrangement can be used to implement the system 100.

The features described with relation to the operational capabilities of the pharmacy management system 100 may be implemented in software running on various hardware platforms. A first pharmacy management computer 200 can be provided for a first pharmacy store, a second pharmacy management computer 300 can be provided for a second pharmacy store, and a third pharmacy management computer 400 can be provided for a third pharmacy store, wherein a pharmacy store may be representative of the exemplary pharmacy 3 described in FIG. 1. Although the pharmacy management system 100 illustrated in FIG. 2 is described herein in terms of being related to three pharmacy stores, it is within the scope of the present invention to include a fewer, or greater, number of pharmacy stores.

The first pharmacy management computer 200 includes a first processing unit 206 comprised of a first processor (not expressly illustrated) and a first memory (not expressly illustrated). The first processing unit 206 may be further comprised of a first pharmacy prescription, patient, and/or medication database 210 and a first pharmacy management software module 220 for performing various pharmacy entry, filling, dispensing, error event prevention/reduction functions, and/or auditing functions as briefly described above, and as will be described in greater detail below. The first pharmacy management computer 200 is in communication with a first input device 230, such as a hand-held or desk-top computer terminal, which is located at the first pharmacy store, for receiving patient information/data, prescription information/data, medication information/data, and other information or data for filling and dispensing medication to patients within the first pharmacy. The first input device 230 transmits the patient information/data, prescription information/data, medication information/data, and/or other information or data to the first pharmacy management computer 200 and to the first pharmacy prescription, patient, and/or medication database 210 for storage therein. Interface screens, described below, are displayed through the first input device for at least receiving the prescription data, and for other functions, which are provided at least in part by the pharmacy management software module 220 from the first pharmacy management computer 200. The first pharmacy management computer 200 may be located at the first pharmacy or elsewhere. For example, the first pharmacy management computer 200 may be an external server in communication with the first input device 230 located within the first pharmacy. Also, although the first pharmacy management computer 200 is illustrated as being in communication with the first input device 230 corresponding to the first pharmacy, it is within the scope of the present invention to include certain embodiments wherein the first pharmacy management computer 200 is in communication with other input devices related to the first pharmacy and/or other pharmacies either illustrated or not specifically illustrated in FIG. 2.

The second pharmacy management computer 300 includes a second processing unit 306 comprised of a second processor (not expressly illustrated) and a second memory (not expressly illustrated). The second processing unit 306 may further be comprised of a second pharmacy prescription, patient, and/or medication database 310 and a second pharmacy management software module 320 for performing various pharmacy entry, filling, dispensing, error event prevention/reduction functions, and/or auditing functions, as briefly described above, and as will be described in greater detail below. The second pharmacy management computer 300 is in communication with a second input device 330, such as a hand-held or desk-top computer terminal, which is located at the second pharmacy store, for receiving patient information/data, prescription information/data, medication information/data, and other information or data for filling and dispensing medication to patients within the second pharmacy. The second input device 330 transmits the patient information/data, prescription information/data, medication information/data, and/or other information or data to the second pharmacy management computer 300 and to the second pharmacy prescription, patient, and/or medication database 310 for storage therein. Interface screens, described below, are displayed through the second input device for at least receiving the prescription data, and for other functions, which are provided at least in part by the pharmacy management software module 320 from the second pharmacy management computer 300. The second pharmacy management computer 300 may be located at the second pharmacy or elsewhere. For example, the second pharmacy management computer 300 may be an external server in communication with the second input device 330 located within the second pharmacy. Also, although the second pharmacy management computer 300 is illustrated as being in communication with the second input device 330 corresponding to the second pharmacy, it is within the scope of the present invention to include certain embodiments wherein the second pharmacy management computer 300 is in communication with other input devices related to the second pharmacy and/or other pharmacies either illustrated or not specifically illustrated in FIG. 2.

Likewise, the third pharmacy management computer 400 includes a third processing unit 406 comprised of a third processor (not expressly illustrated) and a third memory (not expressly illustrated). The third processing unit 406 may further be comprised of a third pharmacy prescription, patient, and/or medication database 410 and a third pharmacy management software module 420 for performing various pharmacy entry, filling, dispensing, error event prevention/reduction functions, and/or auditing functions, as briefly described above, and as will be described in greater detail below. The third pharmacy management computer 400 is in communication with a third input device 430, such as a hand-held or desk-top computer terminal, which is located at the third pharmacy store, for receiving patient information/data, prescription information/data, medication information/data, and other information or data for filling and dispensing medication to patients within the third pharmacy. The third input device 430 transmits the patient information/data, prescription information/data, medication information/data, and/or other information or data to the third pharmacy management computer 400 and to the third pharmacy prescription, patient, and/or medication database 410 for storage therein. Interface screens, described below, are displayed through the third input device for at least receiving the prescription data, and for other functions, which are provided at least in part by the pharmacy management software module 420 from the third pharmacy management computer 400. The third pharmacy management computer 400 may be located at the third pharmacy or elsewhere. For example, the third pharmacy management computer 400 may be an external server in communication with the third input device 430 located within the third pharmacy. Also, although the third pharmacy management computer 400 is illustrated as being in communication with the third input device 430 corresponding to the third pharmacy, it is within the scope of the present invention to include certain embodiments wherein the third pharmacy management computer 400 is in communication with other input devices related to the third pharmacy and/or other pharmacies either illustrated or not specifically illustrated in FIG. 2.

A district, corporate, or central pharmacy management computer 500 may be further provided for centralizing various data and/or for providing functionality which would otherwise be provided by the first, second and/or third pharmacy management computers 200, 300, 400. For instance, at least some of the functionality and/or features of the pharmacy management computers 200, 300, 400, or any other pharmacy management computer included as part of the pharmacy management system 100 may be incorporated into the operational functionality and/or features of the central pharmacy management computer 500 according to some embodiments. It follows that the features described herein may be accomplished by any one of the combinations where the input devices (e.g., 230, 330, 430) are in communication with the pharmacy management computers (e.g., 200, 300, 400) directly, where the input devices (e.g., 230, 330, 430) are in communication with the central pharmacy management computer 500 directly (not expressly illustrated), and where the input devices (e.g., 230, 330, 430) are in communication with the central pharmacy management computer 500 through communication with the pharmacy management computers (e.g., 200, 300, 400). FIG. 2 is illustrated to describe the pharmacy management system 100 being capable of such communication between the components.

As mentioned, the district, corporate or central pharmacy management computer 500 can be provided for centralizing management data and/or for providing functionality which would otherwise be provided by the first, second and/or third pharmacy management computers 200, 300, 400 (can be many others). Specifically, the district, corporate or central pharmacy management computer 500 includes a central processing unit 506 comprised of a central processor and a central memory. The central processing unit 506 may be further comprised of a central pharmacy prescription, patient, and/or medication database 510 and a central pharmacy management software module 520 for performing various pharmacy entry, filling, dispensing, error event prevention/reduction functions, and/or auditing functions as briefly described above and as will be described in greater detail below. In one embodiment, the central pharmacy management computer 500 is in communication with the first, second, and/or third pharmacy management computers 200, 300, 400 for centralizing all or part of the prescription, patient, medication, and other data received, processed, and stored at such computers 200, 300, 400. Alternatively, the information and/or data stored on the pharmacy management computers 200, 300, 400 may be transmitted to the district, corporate or central pharmacy management computer 500 and stored, for example, on the central pharmacy prescription, patient, and/or medication database 510.

According to some embodiments, pharmacy data can be reviewed, tracked and analyzed on a cumulative and other global bases from supervisory terminal devices 550, 570, which can for example be a hand-held or desk-top computer, as will be described in further detail below. Alternatively, the central pharmacy management computer 500 can be directly in communication with first, second, and third input devices 230, 330, 430 (or other similar input devices within the pharmacy management system 100) for receiving and processing pharmacy data for prescriptions, patients, medications, and/or other data received from where the input devices 230, 330, 430 are located, or relating to prescriptions which have been filled or provided to patients through various pharmacies within a multi-store pharmacy enterprise. The input devices 230, 330, 430 may transmit the pharmacy data to the central pharmacy management computer 500 either directly or through other computers or systems, and to the central pharmacy prescription, patient and/or medication database 510 for storage therein. Interface screens, described below, are displayed through the input devices 230, 330, 430 and through supervisory interface devices 550, 570 for at least receiving the pharmacy data, and for other functions, which are provided at least in part by the pharmacy management software modules 520 from the central management computer 500. In one embodiment, the central pharmacy management computer 500 may be located remotely from the pharmacies, and at the corporate or enterprise main offices.

As generally indicated, the system 100 can be implemented in the context of FIG. 1, FIG. 2, or other configurations, in software, as an executable program(s), such as through the software modules 220, 320, 420, 520 including the interface modules therein, executed by one or more processor of a corresponding digital computing device configured to execute the software and execute the operational features of the software as described herein. Examples of such dedicated computing devices may include a personal computer (PC; IBM-compatible, Apple-compatible, or otherwise), personal digital assistant, workstation, minicomputer, server, or mainframe computer.

As mentioned, in terms of hardware architecture shown in FIG. 2, the computer systems and devices mentioned in FIG. 1 and one or more of the computers 200, 300, 400, 500 and input devices 230, 330, 430, 550, 570 mentioned in FIG. 2 may include any combination of a processor, memory, database, software module, as well as one or more input and/or output (I/O) devices communicatively coupled via a communication interface. The communication interface can be, for example, but not limited to, one or more buses or other wired or wireless connections, as is known in the art. The communication interface may have additional elements, which are omitted for simplicity, such as controllers, buffers (caches), drivers, repeaters, and receivers, to enable communications. Further, the interface may include address, control, and/or data connections to enable appropriate communications among the other computer components.

The processors described as being included within the various processing units 206, 306, 406, 506 may be hardware devices for executing software, particularly software stored in a memory, such as the memory described as being included within the various processing units 206, 306, 406, 506. In addition, although input devices 230, 330, 430, 550, and 570 have not been expressly illustrated as including a processor or memory, it should be noted that each of the input devices described herein may include a processor configured to execute software stored on a memory also included in the input device. The processor can be any custom-made or commercially available processor, a central processing unit (CPU), an auxiliary processor among several processors associated with the computers 200, 300, 400, 500 and input/interface devices 230, 330, 430, 550, and 570, a semiconductor-based microprocessor (in the form of a microchip or chip set), a microprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, SQL, Smalltalk, APL, KLisp, Snobol, Developer 200, MUMPS/Magic.

The memory described herein may include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory may incorporate electronic, magnetic, optical, and/or other types of storage media. The memory can have a distributed architecture where various components are situated remote from one another, but are still accessed by the processors. It should be noted that the databases described herein may be a collection of information/data arranged in a known or predictable manner, wherein the information/data is stored on a memory.

The pharmacy management software modules 220, 320, 420, 520 in respective processing units 206, 306, 406, 506 may include one or more separate software programs or modules. In addition, each of the input devices 230, 330, 430, 550, and 570 may also include similar, or like, pharmacy management software modules as described herein. The software programs comprise ordered listings of executable instructions for implementing logical functions that may be executed by the processor included in the corresponding processing units 206, 306, 406, 506, or other processor described herein. In the example of FIG. 1, the software in memory, including memory of input devices 230, 330, 430, 550, 570, also includes a suitable operating system (O/S). A non-exhaustive list of examples of suitable commercially available operating systems is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run-time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). The operating system essentially controls the execution of other software programs by a processor, such as the software programs stored as part of the pharmacy management software modules 220, 320, 420, 520 of system 100, and provides scheduling, input-output control, file and data management, memory management, and communication control and related services.

The software programs that comprise the pharmacy management software modules 220, 320, 420, 520 of system 100 may be a source program, executable program (object code), script, or any other entity comprising a set of instructions to be performed. When using a source program, the program needs to be translated via a compiler, assembler, interpreter, or the like, which may or may not be included within the memory, so as to operate properly in connection with the O/S. Furthermore, the software programs that comprise the pharmacy management software 220, 320, 420, 520 of system 100 may be written as (a) an object-oriented programming language, which has classes of data and methods, or (b) a procedural programming language, which has routines, subroutines, and/or functions, for example but not limited to C, C++, Pascal, Basic, Fortran, Cobol, Perl, Java, and Ada. In one embodiment, the software programs that comprise the pharmacy management software 220, 320, 420, 520 of system 100 may be written in Cow, Java and/or html for use with client type I/O devices.

Each of the computing devices, input devices, and/or other devices described herein as including a processing unit may further include one or more I/O components (i.e., an input output component). The I/O component may, for example, be a keyboard, mouse, scanner, microphone, touch screens, interfaces for various communications devices, barcode readers, stylus, laser readers, radio-frequency device readers, etc. Furthermore, the I/O components may also include output devices, for example but not limited to a printer, barcode printers, displays, etc. Finally, the I/O components may further include devices that communicate both inputs and outputs, for instance but not limited to a modulator/demodulator (modem; for accessing another device, system, or network), a radio frequency (RF) or other transceiver, a telephonic interface, a bridge, a router, and other devices that allow for wired, or wireless, communication of data and/or information.

If the computer 200, 300, 400, 500 and/or input devices 230, 330, 430, 550, 570 is a PC, workstation, PDA, or the like, the software in the memory may further include a basic input output system (BIOS). The BIOS is a set of essential software routines that initialize and test hardware at startup, start the O/S, and support the transfer of data among the hardware devices. The BIOS is stored in ROM so that the BIOS can be executed when the computer is activated.

When computer 200, 300, 400, 500 is in operation, the respective processors are configured to execute software stored within the memory of corresponding processing units 206, 306, 406, 506, to communicate data to and from corresponding memory, and to generally control operations of the respective computer(s) 200, 300, 400, 500, pursuant to the software. The software programs that comprise the pharmacy management software modules 220, 320, 420, 520 of system 100, and the O/S, in whole or in part, but typically the latter, are read by processor(s), perhaps buffered within the processor, and then executed.

It should be noted that the software programs that comprise the pharmacy management software modules 220, 320, 420, 520 can be stored on any computer-readable medium for use by or in connection with any computer-related system or method. In the context of this disclosure, a computer readable medium is an electronic, magnetic, optical, or other physical device or means that can contain or store a computer program for use by or in connection with a computer related system or method. The pharmacy management software modules 220, 320, 420, 520 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this disclosure, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable media would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Specifically, the pharmacy management software modules 220, 320, 420, 520 of system 100 may be comprised of at least one of a data entry module, a data review module, and a prescription dispensing and/or filling module, for at least entry review and/or dispensing/filling a prescription having prescription information. One or more of these software modules and/or other software modules include code for identifying, preventing, and/or checking for errors that may be made during the prescription dispensing process in order to prevent, or at least reduce, a chance that the wrong medication is dispensed or taken by a customer.

As a side note, a detailed organizational hierarchy can be stored and utilized for these and other functions within one or more of the pharmacy databases 210, 310, 410, 510, for use within the pharmacy management system 100. As mentioned above, there are various different players or personnel in a pharmacy and in a pharmacy enterprise or organization. At each pharmacy store, there are one or more technicians (Tx or Tech) who receive prescriptions, enter prescriptions into the pharmacy management system 100, pick prescriptions, and fill prescriptions. Each pharmacy also has one or more pharmacists (Rx) who also are involved with prescription filling, at least in checking the accuracy of the filling of the prescription before being provided to the patient. A store manager (SM) and a pharmacy supervisor (RxS) are additional personnel within each pharmacy store. Pharmacy supervisors (RxS) can also be "located" at the district level. A district manager (DM) or pharmacy supervisor (RxS) can be responsible for two or more stores which can be classified as a district. Regional managers (RM) can also be involved in the process described herein and are responsible for two or more districts which make up such region. Quality assurance (QA) and/or personnel at the corporate level are responsible for all of the regions, districts, and stores and are also involved in the process described herein.

The pharmacy management computers, software modules, and databases are utilized throughout the process of receiving, filling and dispensing prescriptions, including some automated checking of whether a prescription order has been correctly filled, as indicated above.

Figure 3:
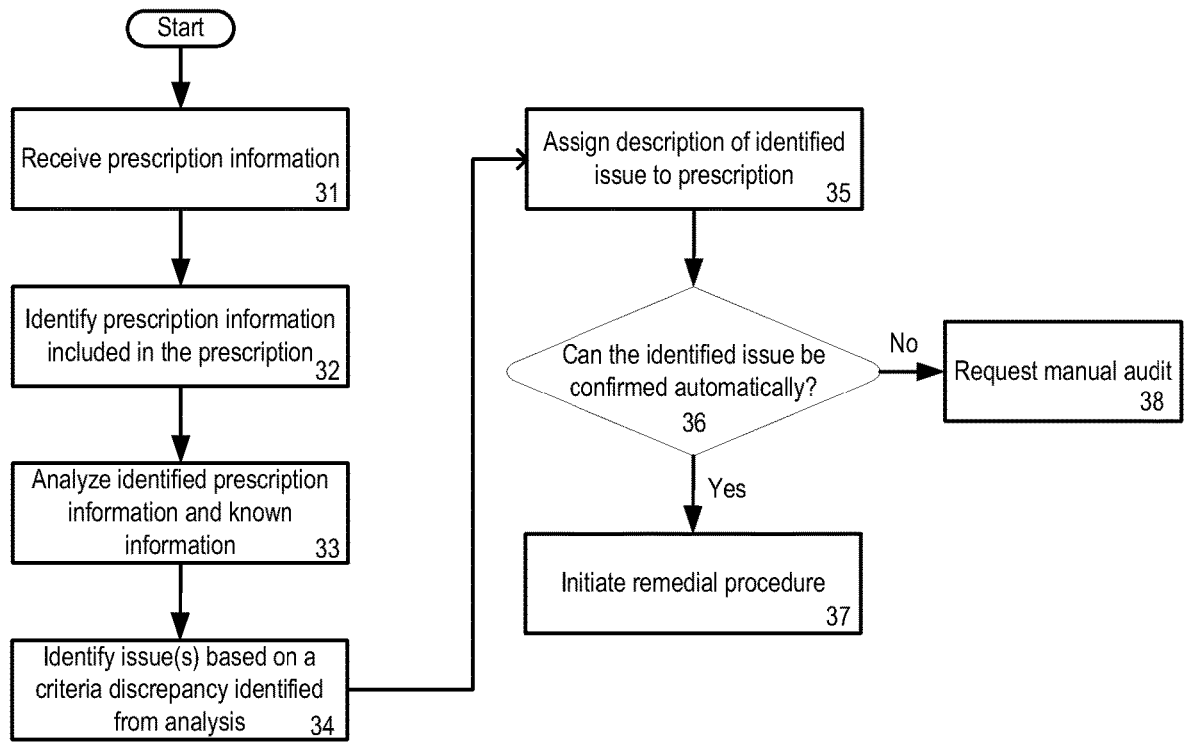
FIG. 3 illustrates a flow chart describing an exemplary process for auditing a prescription filling process, according to some embodiments.

Further description for the checking process will be provided with respect to flow chart 30 illustrated in FIG. 3. The flow chart 30 illustrated in FIG. 3 describes a process for auditing a prescription filling process that may be currently executed at a pharmacy (i.e., medication from the prescription may not have been released to the customer yet). The steps described within flow chart 30 will be described in terms of one or more computing devices operating in communication with each other to implement the features described by flow chart 30. The computing devices may, for example, correspond to any one or more of the input device 230, 330, 430, 550, 570 pharmacy management computer 200, 300, 400, central pharmacy management computer 500, or any of the other computing devices described herein. The computing devices may operate to implement the features described within flow chart 30 according to a processor executing software instructions stored on a memory of the computing device. In this way, the computing devices may be especially configured to implement the auditing features described within the steps of flow chart 30 as described herein.

At 31, prescription information may be received at a pharmacy. For example, a customer may hand a pharmacist, or other pharmacy employee, a prescription document that identifies one or more medications to be dispensed by the pharmacy to the customer. The prescription may also include notes written by the prescribing medical professional, as well as consumption details for aiding the customer when taking the medication described in the prescription. The prescription may also include billing information and/or billing criteria information that identifies an appropriate billing method for processing the prescription. The pharmacist may directly input the information described in the prescription (i.e., the prescription information) into a pharmacy computing device (e.g., the filling/checking workstation 11 illustrated in FIG. 1) in order for the pharmacy computing device to receive the prescription information. For example, the prescription information may be inputted via manual input through a keyboard, mouse, touchpad, or other type of I/O component that may be in communication with the pharmacy computing device.

According to some embodiments, the pharmacy computing device may have alternatively received the pharmacy information from another computing device within the pharmacy. For example, the pharmacy computing device may have received the prescription information from another computing device within the pharmacy where the prescription information was previously inputted (e.g., order entry workstation 9 illustrated in FIG. 1). It follows then that the prescription information may have been directly inputted into the other computing device previously, then transmitted by the other computing device via a communications network (e.g., internet, WiFi, LAN, telecommunications network, or other type of communications network that allows for wired or wireless communication of information) to the pharmacy computing device, such that the pharmacy computing device ultimately receives the pharmacy information through a communication interface of the pharmacy computing device. The communication interface may allow for wired and/or wireless communication between computing devices.

According to some embodiments, the pharmacy computing device may have alternatively received the pharmacy information from another computing device not within the pharmacy. In such embodiments, the pharmacy computing device may correspond to a computing device within a pharmacy management system (e.g., pharmacy management system 100). The pharmacy computing device may receive the prescription information from a customer's personal computing device (e.g., customer's personal computer) located outside of the physical pharmacy and/or not within the pharmacy management system. The customer may have input the prescription information into the customer's computing device, transmitted the prescription information via a communications network (e.g., internet, WiFi, LAN, telecommunications network, or other type of communications network that allows for wired or wireless communication of information) to the pharmacy computing device, wherein the pharmacy computing device received the prescription network transmitted via the communications network through a communications interface of the pharmacy computing device. Although the example of the customer's personal computing device is given, it is within the scope of the invention described herein for the computing device outside of the pharmacy to be another computing device such as a computing device corresponding to a hospital or other medical institution such that a medical professional located at the hospital or other medical intuition transmits the prescription information to the pharmacy computing device.

At 32, the pharmacy computing device may analyze the received prescription information in order to determine one or more medications included in the customer's prescription as identified prescription information. The analysis at 32 may additionally determine any additional information that may have been included on the customer's prescription as identified prescription information, as described above.

According to some embodiments, the pharmacy computing device located at the pharmacy may transmit the received prescription information to an offsite server computing device for analysis of the prescription information. For example, the pharmacy computing device may transmit the prescription information to an offsite server computing device such as to a pharmacy management computer corresponding to the pharmacy (e.g., pharmacy management computers 200, 300, 400), or directly to a central pharmacy management computer (e.g., central pharmacy management computer 500). The prescription information may be transmitted from the pharmacy computing device to the offsite server computing device through the communications interface of the pharmacy computing device and via a communications network (e.g., internet, WiFi, LAN, telecommunications network, or other type of communications network that allows for wired or wireless communication of information). The prescription information transmitted via the communications network may then be received by the offsite server computing device through a communications interface of the offsite server computing device. The offsite server computing device may then analyze the prescription information in order to identify one or more medications described in the customer's prescription, as well as to identify any additional information that may have been included on the customer's prescription, as described above.

At 33, the computing device may analyze the identified prescription information from 32 and also analyze known information. For example, the computing device may compare the identified prescription information from 32 against known information at 33. The analysis at 33 may, for example, also include analyzing the identified prescription information to compare a medication identified from the identified prescription information and instructions for taking the medication also identified from the identified prescription information. In addition or alternatively, the analysis at 33 may, for example, include analyzing the identified prescription information to compare instructions for taking a medication identified from the identified prescription information against known information that may describe acceptable, known, and/or safe ways for taking the medication. In addition or alternatively, the analysis at 33 may, for example, include analyzing billing information from the prescription information and/or known information in order to determine a billing process that has occurred, or is occurring, with relation to the prescription filled, or currently being filled. The billing information may then be compared against a billing protocol stored within the known information in order to determine whether the billing process that has occurred, or is occurring, is the correct billing process for the prescription.

The known information may include customer profile information that includes historical information detailing past prescriptions filled by the customer, as well as customer attribute information that may include information identifying the customer's name, age, date of birth, weight, height, known medical conditions, known allergies, past medical procedures, and other information related to the customer's identification and/or medical health profile. The known information may also include a database of known medical reactions when two or more different medications are taken together or within a certain timeframe. The known information may also include a database of suggested, known to be safe, and/or known to be acceptable dosage levels for certain medications in view of attributes of the user (e.g., age, date of birth, weight, height, known medical conditions, known allergies, past medical procedures, and other information related to the user's identification and/or health). The known information may also include a database of billing protocols that identifies an appropriate billing protocol for a specific patient, medication, doctor, or other identification that may be included on a prescription.

The known information may be stored and accessed from a memory of the computing device located at the pharmacy (e.g., data entry workstation 9 or filling/checking workstation 11), or at a memory of a computing device outside of the pharmacy such as the offsite server computing device (e.g., pharmacy management computer 200, 300, 400, or central pharmacy management computer 500).

Alternatively, according to some embodiments where the pharmacy computing device identified the medications and/ or other information included on the customer's prescription at 32, the pharmacy computing device may transmit the identified prescription information to the offsite server computing device at 33 so that the offsite computing device may further compare the identified prescription information against known information at 33.

At 34, the computing device having implemented the comparison analysis at 33, may identify an issue based on a criteria or rule discrepancy identified from the analysis of the identified prescription information and the known information. Steps 33 and 34 in flow chart 30 may be considered the auditing steps. For example, based on a comparison of the identified prescription information and the customer's medical history information at 33, the computing device may determine an issue exists at 34 that one or more medications identified in the identified prescription information has never been prescribed to the particular customer previously. When such a determination is made by the computing device at 34, the process may proceed to 36 where a description of the issue is assigned to the prescription. According to some embodiments, if no issues are identified at 34, the computing device may allow the prescription filling process to continue if the auditing steps are occurring at the same time the prescription is being filled, or alternatively, the computing device may simply not raise any flags if the auditing steps are occurring after the filling process has finished previously.

In addition or alternatively, based on the analysis of the identified prescription information and the known information at 33, the computing device may determine an issue exists at 34 that the instructions for taking one or more medications identified in the identified prescription information is not correct, or at least does not match instructions found in the known information. When such a determination is made by the computing device at 34, the process may proceed to 35 where a description of the issue is assigned to the prescription.

In addition or alternatively, based on the analysis of the identified prescription information, customer's profile information, and/or other known information at 33, the computing device may determine an issue exists at 34 that the instructions for taking one or more medications identified in the identified prescription information is not correct for a person that fits one or more attributes of the customer as identified from the customer's profile information (e.g., instructions for taking the same medication may be different for people of different ages, weight, height, medical condition, etc.). When such a determination is made by the computing device at 34, the process may proceed to 35 where a description of the issue is assigned to the prescription.

In addition or alternatively, based on the analysis of the identified prescription information and the known information at 33, the computing device may determine an issue exists at 34 that instructed dosages for taking one or more medications identified in the identified prescription information is not correct. When such a determination is made by the computing device at 34, the process may proceed to 35 where a description of the issue is assigned to the prescription.

In addition or alternatively, based on the analysis of the identified prescription information, customer's profile information, and/or other known information at 33, the computing device may determine an issue exists at 34 that instructed dosages for taking one or more medications identified in the identified prescription information is not correct for a person that fits one or more attributes of the customer as identified from the customer's profile information (e.g., dosages for the same medication may be different for people of different ages, weight, height, medical condition, etc.). When such a determination is made by the computing device at 34, the process may proceed to 35 where a description of the issue is assigned to the prescription.

In addition to the exemplary issues that may be identified during the audit step at 34, the computing device may further look to identify an issue where one or more audit rules have been violated. For example, Table 40, as illustrated in FIGS. 4-10, describes a number of exemplary audit rules. Table 40 further includes a description for a situation that may cause an audit to flag the audit rules may have been violated. The Table 40 may be stored within any one or more of the memory storage units described herein as being included in any one or more of the computing devices described herein, so that a processor of the computing device may have access to the Table 40 during the implementation of the processes that are a part of flow chart 30. It follows that an analysis of the identified prescription information and the known information at 33 may allow for the determination that an issue is identified in the form of an audit rule being violated.

As described above, when an issue is identified at 34, the process described by flow chart 30 may proceed to 35 where a description of the identified issue may be assigned to the prescription. For example, a description of the identified issue may be included with the prescription information corresponding to the customer's prescription.

At 36, a computing device having implemented the comparison analysis at 36 may make a determination as to whether the identified issue can be confirmed automatically. In other words, an analysis may be implemented on the identified issue, identified prescription information, and/or known information to determine whether the identified issue could only result in a violation of an audit rule or other error that should be flagged, as described herein. If the analysis at 36 determines that the identified issue could, but does not necessarily result, in the violation of an audit rule or other error be present, then at 38 a manual audit may be requested. For example, if a medication identified from the identified prescription information is known for typically being recommended for being taken through a first method (e.g., oral ingestion) but the instructions from the identified prescription information is found to instruct the customer to take the medication according to a second method (e.g., apply medication topically) which is not the recommended method, but not erroneous (i.e., the medication may be taken according to the second method, although not typically recommend to be taken this way), then a manual audit may be requested at 38 to further look into the discrepancy and verify that the medication and the instructed method for taking the medication are correct.

According to another example, the identified issue from 34 may correspond to a dosage for a medication identified from the prescription information that is recognized to be higher than historically prescribed for the customer, yet still within an acceptable range based on known information. In such a scenario where the identified issue has recognized a discrepancy that cannot be confirmed automatically as an error or violation of an audit rule, a manual audit may be requested at 38 to further look into the discrepancy and verify that the medication and the instructed method for taking the medication are correct.

The request for manual audit at 38 may require the pharmacist, or other pharmacy employee, to complete a manual verification of the information on the prescription before allowing the medication from being dispensed to the customer. According to some embodiments, the pharmacy computing device may prevent further operation until the pharmacist has at least acknowledged the request for manual audit. For embodiments where the server computing device implements the determination process at 36, a request signal may be transmitted from the server computing device to the pharmacy computing device so that the pharmacy computing device may request the manual audit to be performed. The information describing the steps for the manual audit procedure may be accessible by the pharmacy computing device from a memory of the pharmacy computing device, or from a memory of an offsite server computing device in communication with the pharmacy computing device.

A determination at 36 that the identified issue can be confirmed automatically may involve an analysis that determines, for example, the identified issue could only result in a violation of a rule or other error that should be flagged, as described herein. For example, if a medication identified from the identified prescription information is known for only being taken through a first method (e.g., oral ingestion) and the instructions identified from the identified prescription information is found to instruct the customer to take the medication according to a second method (e.g., apply medication topically) that is determined by an analysis of known information not to be a known, acceptable, or safe method for taking the medication, the computing device may determine that the identified issue can be confirmed automatically.

When a determination is made at 36 that the identified issue can be confirmed automatically, then at 37 a remedial procedure may be initiated.

The remedial procedure initiated at 37 may be dependent on the particular issue identified at 34. For example, when a determination is made at 34 that one or more medications identified in the identified prescription information has never been prescribed to the particular customer previously, the remedial procedure initiated at 37 may include prompting a message to be displayed at the pharmacy inquiring whether the medication identified from the identified prescription information is the intended medication prescribed to the customer. The message may be generated based on the determination at 34 and subsequently presented to the pharmacist at the pharmacy via a display at a computing device available at the pharmacy. In some embodiments, the pharmacist may not be able to proceed with the dispensing of the medications described in the customer's prescription until verification is made. The verification may be implemented by the pharmacist by, for example, inquiring the customer directly as to whether the medication identified from the identified prescription information is indeed correct for the customer. The verification may also be implemented by the pharmacist by, for example, inquiring the medical professional as to whether the medication identified from the identified prescription information is indeed correct for the customer. After a verification completion signal is input to the pharmacy computing device following a successful verification, the prescription filling process may proceed. According to some embodiments, the pharmacy computing device may prevent further operation until the pharmacist has at least acknowledged the request for verification.

The remedial procedure initiated at 37 may be dependent on the issue identified at 34. For example, when a determination is made by the computing device at 34 that the instructions for taking one or more medications identified in the identified prescription information is not correct, or at least does not match instructions found in the known information, the remedial procedure initiated at 37 may include prompting a message to be displayed at the pharmacy that describes instructions for taking the one or more medications based on the instructions found in the known information. The message may be generated based on the determination at 34 and subsequently presented to the pharmacist at the pharmacy via a display at a computing device available at the pharmacy. In some embodiments, the pharmacist may not be able to proceed with the dispensing of the medications described in the customer's prescription until verification is made. The verification may be implemented by the pharmacist by, for example, inputting a verification that the customer has been presented with the correct instructions for taking the one or more medications. The verification may, in addition or alternatively, also require the pharmacist to verify that a medical professional responsible for the customer's prescription has been contacted in order to verify the correct instructions for taking the one or more medications. After a verification completion signal is input to the pharmacy computing device following a successful verification, the prescription filling process may proceed. According to some embodiments, the pharmacy computing device may prevent further operation until the pharmacist has at least acknowledged the request for verification.

The remedial procedure initiated at 37 may be dependent on the issue identified at 34. For example, when a determination is made by the computing device at 34 that the instructions for taking one or more medications identified in the identified prescription information is not correct, the remedial procedure initiated at 37 may include prompting a message to be displayed at the pharmacy that describes the correct instructions for taking the one or more medications based on the instructions described in the known information. The message may be generated based on the determination at 34 and subsequently presented to the pharmacist at the pharmacy via a display at a computing device available at the pharmacy. In some embodiments, the pharmacist may not be able to proceed with the dispensing of the medications described in the customer's prescription until verification is made. The verification may be implemented by the pharmacist by, for example, inputting a verification that the customer has been presented with the correct instructions for taking the one or more medications. The verification may, in addition or alternatively, also require the pharmacist to verify that a medical professional responsible for the customer's prescription has been contacted in order to verify the correct instructions for taking the one or more medications. After a verification completion signal is input to the pharmacy computing device following a successful verification, the prescription filling process may proceed. According to some embodiments, the pharmacy computing device may prevent further operation until the pharmacist has at least acknowledged the request for verification.

The remedial procedure initiated at 37 may be dependent on the issue identified at 34. For example, when the determination is made by the computing device at 34 that the instructed dosages for taking one or more medications identified in the identified prescription information is not correct, the remedial procedure initiated at 37 may include prompting a message to be displayed at the pharmacy that describes the correct dosages for taking the one or more medications based on the dosages described in the known information. The message may be generated based on the determination at 34 and subsequently presented to the pharmacist at the pharmacy via a display at a computing device available at the pharmacy. In some embodiments, the pharmacist may not be able to proceed with the dispensing of the medications described in the customer's prescription until verification is made. The verification may be implemented by the pharmacist by, for example, inputting a verification that the customer has been presented with the correct dosage instructions for taking the one or more medications. The verification may, in addition or alternatively, also require the pharmacist to verify that a medical professional responsible for the customer's prescription has been contacted in order to verify the correct dosages for taking the one or more medications. After a verification completion signal is input to the pharmacy computing device following a successful verification, the prescription filling process may proceed. According to some embodiments, the pharmacy computing device may prevent further operation until the pharmacist has at least acknowledged the request for verification.

The remedial procedure initiated at 37 may be dependent on the issue identified at 34. For example, when the determination is made by the computing device at 34 that the instructed dosages for taking one or more medications identified in the identified prescription information is not correct, the remedial procedure initiated at 37 may include prompting a message to be displayed at the pharmacy that describes the correct dosages for taking the one or more medications based on the dosages described in the known information. The message may be generated based on the determination at 34 and subsequently presented to the pharmacist at the pharmacy via a display at a computing device available at the pharmacy. In some embodiments, the pharmacist may not be able to proceed with the dispensing of the medications described in the customer's prescription until verification is made. The verification may be implemented by the pharmacist by, for example, inputting a verification that the customer has been presented with the correct dosage instructions for taking the one or more medications. The verification may, in addition or alternatively, also require the pharmacist to verify that a medical professional responsible for the customer's prescription has been contacted in order to verify the correct dosages for taking the one or more medications. After a verification completion signal is input to the pharmacy computing device following a successful verification, the prescription filling process may proceed. According to some embodiments, the pharmacy computing device may prevent further operation until the pharmacist has at least acknowledged the request for verification.

The remedial procedure initiated at 37 may be dependent on the issue identified at 34. For example, if a determination is made at 34 that a medication identified from the identified prescription information is known for being taken through a first method (e.g., oral ingestion) and the instructions identified from the identified prescription information is found to instruct the customer to take the medication according to a second method (e.g., apply medication topically) that is determined by an analysis of known information not to be a known, acceptable, or safe method for taking the medication, the computing device may initiate a remedial procedure at 37. The remedial procedure initiated at 37 may correspond to any one or more of the remedial procedures described herein. For instance, the remedial procedure initiated at 37 may require the pharmacist, or other pharmacy employee, to complete a manual verification of the information on the prescription before allowing the medication from being dispensed to the customer. According to some embodiments, the pharmacy computing device may prevent further operation until the pharmacist has at least acknowledged the request for verification.

As another example, if instructions for taking the medication as identified from the identified prescription information are determined not to correspond to any of the known, acceptable, or safe methods for taking the medication as described in the known information, the computing device may initiate a remedial procedure at 37. The remedial procedure initiated at 37 may correspond to any one or more of the remedial procedures described herein. For instance, the remedial procedure initiated at 37 may require the pharmacist, or other pharmacy employee, to complete a manual verification of the information on the prescription before allowing the medication from being dispensed to the customer. According to some embodiments, the pharmacy computing device may prevent further operation until the pharmacist has at least acknowledged the request for verification.

The remedial procedure initiated at 37 may be dependent on the issue identified at 34. For example, if a determination is made at 34 that a billing process that has occurred, is occurring concurrently, or will be implemented with reference to the prescription is found not to be in compliance with an appropriate billing protocol, the computing device may initiate a remedial procedure at 37. The remedial procedure initiated at 37 may correspond to any one or more of the remedial procedures described herein. For instance, the remedial procedure initiated at 37 may generate an alert that identifies that the appropriate billing protocol is not being implemented for the prescription. The remedial procedure at 37 may further require the pharmacist, or other pharmacy employee, to complete a manual verification that the discrepancy with the billing protocol will be addressed. According to some embodiments, the pharmacy computing device may prevent further operation until the pharmacist has at least acknowledged the request for verification.

In addition or alternatively, the remedial procedure initiated at 37 in response to identifying an issue at 34 may be to disregard the customer's prescription. In other words, the pharmacy may flag the issue identified at 34 as an issue that will prevent the pharmacy computing device from further proceeding to allow dispensing of the medication(s) identified in the customer's prescription from being dispensed. In some embodiments where the customer's prescription includes more than one medication, only medications having an identified issue at 34 may be disregarded. In some embodiments, identifying one issue with one medication may result in the entire prescription from being disregarded even if other medications are not found to have an issue.

It should be noted that the steps described with respect to the audit process of flow chart 30 is provided for exemplary purposes only, as it is within the scope of the present invention to encompass other embodiments that may include a fewer, or greater, number of steps for implementing an audit process for verifying a prescription may be dispensed to a customer.

According to some embodiments the audit procedure corresponding to flow chart 30 that describes a process for auditing a prescription filling process that may be currently executed at a pharmacy, may further be applicable to an audit process that may be executed at the pharmacy after the prescription has been dispensed. For instance, the audit process described by flow chart 30 may also be applicable to an audit process that may be executed at certain time(s) (e.g., end of business audit procedure) after the prescription has been filled and/or dispensed to the customer. For instance, the audit process described by flow chart 30 may be implemented after a customer's prescription has been filled and/or dispensed in order to provide a verification check that previously dispensed medications were dispensed correctly. In some embodiments, the detailed audit process described by flow chart 30 may not be available, or may be too cumbersome to implement, at the time of filling the customer's prescription. Therefore, the application of the audit process described by flow chart 30 after the prescription has been dispensed may offer a more detailed audit verification check for the pharmacy.

In such embodiments where the audit process is implemented after filling and/or dispensing a customer's prescription, the process in flow chart 30 may additionally include remedial procedures at 37 that includes contacting the customer when a medication dispensed to the customer is found to satisfy any one or more of the errors, issues, and/or discrepancies identified at 34. For instance, the pharmacy computing device may alert the pharmacist, or other pharmacy employee, that an issue and/or discrepancy was identified at 34, and require the pharmacist, or other pharmacy employee, to verify that the customer has been contacted and alerted. According to some embodiments, the pharmacy computing device may prevent further operation until such verification is provided to the pharmacy computing device that the customer has been contacted, or that the pharmacist has at least acknowledged the alert.

The process in flow chart 30 has been described as being implemented by certain computing device(s) within, for example, a system such as pharmacy management system 100 illustrated in FIG. 2. It follows that any one or more of the computers and/or input devices described as being within pharmacy management system 100 may be responsible for implementing any one or more of the steps described in the process of flowchart 30.

Any process descriptions or blocks in the figures, should be understood as representing modules, segments, or portions of code which include one or more executable instructions for implementing specific logical functions or steps in the process, and alternate implementations are included within the scope of the embodiments described herein, in which functions may be executed out of order from that shown or discussed, including substantially concurrently or in reverse order, depending on the functionality involved, as would be understood by those having ordinary skill in the art.

It should be emphasized that the above-described embodiments, particularly, any "preferred" embodiments, are possible examples of implementations, merely set forth for a clear understanding of the principles of the invention. Many variations and modifications may be made to the above-described embodiment(s) without substantially departing from the spirit and principles of the techniques described herein. All such modifications are intended to be included herein within the scope of this disclosure and protected by the following claims.

What is claimed is:

1. A computing device for auditing a prescription filling order of a prescription processed by an order filling device located at a pharmacy, comprising:
   a communication interface configured to receive prescription information from the order filling device via a communications network, the prescription information describing information having been identified by the pharmacy and inputted into the order filling device, the prescription information describing information included in the prescription of the prescription filling order that identifies at least one of a medication to be dispensed by the pharmacy to a specific customer and instructions for taking the medication, wherein the instructions include routes of administration;
   a memory configured to store known information, wherein the known information comprises an audit rule and acceptable instructions for the medication in view of a medical health profile of the specific customer, wherein the medical health profile includes known medical conditions or past medical procedures pertaining to the specific customer; and
   a processor in communication with the communication interface and memory, the processor configured to automatically perform a two-stage audit of the prescription filling order by:
      obtaining the acceptable instructions and the audit rule, wherein the audit rule defines unacceptable instructions for taking the medication that is known for being taken through a first route of administration through a second route of administration;
      obtaining the identified instructions for taking the identified medication;
      determining that the identified instructions cannot be automatically confirmed by evaluating that the identified instructions does not match the acceptable instructions at a first stage of the two-stage audit;
      in response to determining that the identified instructions cannot be automatically confirmed, determining that the identified instructions can be automatically confirmed by evaluating that the identified instructions matches the second route of administration provided by the audit rule at a second stage of the two-stage audit;
      generating an auditing flag in response to determining that the identified instructions can be automatically confirmed; and
      transmitting, in response to the generated auditing flag, an instruction signal to the order filling device through the communication interface, wherein the order filling device is prevented from dispensing of the identified medication in the prescription until a verification completion signal is input to the order filling device.

2. The computing device of claim 1, wherein the prescription information includes at least one of instructional information describing medication usage instructions for taking one or more medications identified in the prescription information, or dosage information describing medication dosage instructions for one or more medications identified in the prescription information.

3. The computing device of claim 1, wherein the instruction signal provides an indication for the prescription filling order to, at least temporarily, not proceed with the prescription filling order.

4. The computing device of claim 1, wherein the known information further comprises at least one of known recommended medication dosage information, known recommended medication usage information, know medication reaction information, or known medication recommended therapy information.

5. The computing device of claim 1, wherein the processor is configured to generate the auditing flag when an analysis between the prescription information and the known information identifies a discrepancy between the medication described in the prescription information and prescription filling history information for the customer described in the known information.

6. The computing device of claim 1, wherein the processor is configured to generate the auditing flag when an analysis between the prescription information and the known information identifies a discrepancy between instructions for taking the medication described in the prescription information and recommended medication usage information described in the known information.

7. The computing device of claim 1, wherein the processor is configured to generate the auditing flag when an analysis between the prescription information and the known information identifies a discrepancy between dosage information for the medication described in the prescription information and recommended medication dosage information described in the known information.

8. The computing device of claim 1, wherein
the instruction signal includes instructions for implementing a remedial procedure that includes generating a message describing the auditing flag, controlling a display of the auditing flag, and requiring an acknowledgement input to be received before the prescription filling order is allowed to proceed.

9. The computing device of claim 1, wherein the processor is further configured to prompt a message to be displayed at the pharmacy that further describes the acceptable instructions described in the known information.

10. A method for auditing a prescription filling order of a prescription processed by an order filling device located at a pharmacy, comprising:
obtaining, by an information obtaining component in communication with the order filling device at the pharmacy, prescription information included in a prescription order, the prescription information describing information having been identified by the pharmacy and inputted into the order filling device;
storing, on a memory of the order filling device, the prescription information;
transmitting, by the order filling device, the prescription information to an auditing computing device;
automatically performing, by the auditing computing device, a two-stage audit of the prescription filling order by:
receiving, by the auditing computing device, the prescription information from the order filling device through a communication interface via a communications network, the prescription information describing information included in the prescription of the prescription filling order that identifies at least one of a medication to be dispensed by the pharmacy to a specific customer and instructions for taking the medication, wherein the instructions include routes of administration;
obtaining, by the auditing computing device, known information stored on a memory of the auditing computing device, wherein the known information comprises an audit rule and acceptable instructions for the medication in view of a medical health profile of the specific customer, wherein the audit rule defines unacceptable instructions for taking the medication that is known for being taken through a first route of administration through a second route of administration, wherein the medical health profile includes known medical conditions or past medical procedures pertaining to the specific customer;
determining, by the auditing computing device, that the identified instructions cannot be automatically confirmed by evaluating that the identified instructions does not match the acceptable instructions at a first stage of the two-stage audit;
in response to determining that the identified instructions cannot be automatically confirmed, determining, by the auditing computing device, that the identified instructions can be automatically confirmed by evaluating that the identified instructions matches the second route of administration provided by the audit rule at a second stage of the two-stage audit;
generating, by the auditing computing device, an auditing flag in response to determining that the identified instructions can be automatically confirmed; and
transmitting, by the auditing computing device, in response to the generated auditing flag, an instruction signal to the order filling device through the communication interface, wherein the order filling device is prevented from dispensing of the identified medication in the prescription until a verification completion signal is input to the order filling device.

11. The method of claim 10, wherein the instruction signal provides an indication for the prescription filling order to, at least temporarily, not proceed with the prescription filling order.

12. The method of claim 10, wherein generating the auditing flag occurs when an analysis between the prescription information and the known information identifies a discrepancy between the medication described in the prescription information and prescription filling history information for the customer described in the known information.

13. The method of claim 10, wherein generating the auditing flag occurs when an analysis between the prescription information and the known information identifies a discrepancy between instructions for taking the medication described in the prescription information and recommended medication usage information described in the known information.

14. The method of claim 10, wherein the instruction signal includes instructions for implementing a remedial procedure that includes generating a message describing the auditing flag, controlling a display of the auditing flag, and requiring an acknowledgement input to be received before the prescription filling order is allowed to proceed.

15. A system for auditing a prescription filling order of a prescription, comprising:
a computing device at the pharmacy for auditing prescription orders; and
an input device for filling prescription orders, configured to:
transmit prescription information to the computing device via a communications network, the prescription information describing information having been identified by the pharmacy and inputted into the input device, wherein the computing device is configured to automatically perform a two-stage audit of the prescription filling order, wherein the computing device is configured to:
receive the prescription information through a communication interface, the prescription information describing information included in the prescription of the prescription filling order that identifies at least one of a medication to be dispensed by the pharmacy to a specific customer and instructions for taking the medication, wherein the instructions include routes of administration;
access known information from a memory, wherein the known information comprises an audit rule and acceptable instructions for the medication in view of a medical health profile of the specific customer, wherein the audit rule defines unacceptable instructions for taking the medication that is known for being taken through a first route of administration through a second route of administration, wherein the medical health profile comprises known medical conditions or past medical procedures pertaining to the specific customer;

analyze the prescription information and the known information to at least one of: determine whether the instructions for taking the medication identified in the prescription information is correct for the customer according to the medical health profile of the customer; or determine whether the billing process that has occurred, or is occurring, with relation to the prescription filled, or currently being filled is the correct billing process for the prescription according to the billing protocol;

determine that the identified instructions cannot be automatically confirmed by evaluating that the identified instructions does not match the acceptable instructions at a first stage of the two-stage audit;

in response to a determination that the identified instructions cannot be automatically confirmed, determine that the identified instructions can be automatically confirmed by evaluating that the identified instructions matches the second route of administration provided by the audit rule at a second stage of the two-stage audit;

generate an auditing flag in response to determining that the identified instructions can be automatically confirmed; and transmit, in response to the generated auditing flag, an instruction signal to the input device through the communication interface, wherein the input device is prevented from dispensing of the identified medication in the prescription until a verification completion signal is input to the input device.

16. The system of claim 15, wherein the computing device is further configured to prompt a message to be displayed at the pharmacy that further describes the acceptable instructions described in the known information.

17. The computing device of claim 1, wherein the first route of administration and the second route of administration comprise oral ingestion and topical application, respectively.

18. The method of claim 10, wherein the first route of administration and the second route of administration comprise oral ingestion and topical application, respectively.

19. The system of claim 15, wherein the first route of administration and the second route of administration comprise oral ingestion and topical application, respectively.

* * * * *